(12) United States Patent
Berman et al.

(10) Patent No.: US 7,743,648 B1
(45) Date of Patent: Jun. 29, 2010

(54) SPIN MICROSCOPE BASED ON OPTICALLY DETECTED MAGNETIC RESONANCE

(75) Inventors: Gennady P. Berman, Los Alamos, NM (US); Boris M. Chernobrod, Los Alamos, NM (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 377 days.

(21) Appl. No.: 11/845,982

(22) Filed: Aug. 28, 2007

(51) Int. Cl.
*G01V 3/00* (2006.01)
(52) U.S. Cl. ........................................................ 73/105
(58) Field of Classification Search .................. None
See application file for complete search history.

(56) References Cited

U.S. PATENT DOCUMENTS 5,479,024 A * 12/1995 Hillner et al. ............. 250/458.1

OTHER PUBLICATIONS

D. Rugar, C.S. Yannoini, and J.A. Sidles, Nature, 360, 563, Reference [1], Dec. 1992.*
G.T. Shubeita, S.K. Seikatskii, G Dietler, and V.S. Letokohov, Appl. Phys. Lett. 80, 2625-2627, Reference [6], Apr. 2002.*

* cited by examiner

*Primary Examiner*—Robert R Raevis
(74) *Attorney, Agent, or Firm*—Thomas S. O'Dwyer; James C. Durkis

(57) ABSTRACT

The invention relates to scanning magnetic microscope which has a photoluminescent nanoprobe implanted in the tip apex of an atomic force microscope (AFM), a scanning tunneling microscope (STM) or a near-field scanning optical microscope (NSOM) and exhibits optically detected magnetic resonance (ODMR) in the vicinity of unpaired electron spins or nuclear magnetic moments in the sample material. The described spin microscope has demonstrated nanoscale lateral resolution and single spin sensitivity for the AFM and STM embodiments.

1 Claim, 5 Drawing Sheets

US 7,743,648 B1

SPIN MICROSCOPE BASED ON OPTICALLY DETECTED MAGNETIC RESONANCE

STATEMENT REGARDING FEDERALLY SPONSORED RESEARCH OR DEVELOPMENT

The U.S. Government has a paid-up license in this invention and the right in limited circumstances to require the patent owner to license others in reasonable terms as provided for by the terms of Contract No. W-7405-ENG-36 awarded by the U.S. Department of Energy and Los Alamos National Laboratory.

CROSS-REFERENCE TO RELATED APPLICATION

This application claims priority from U.S. provisional application Ser. No. 60/560,979 filed on Apr. 12, 2004.

BACKGROUND OF THE INVENTION

1. Field of the Invention (Technical Field)

The present invention relates to a scanning magnetic microscope based on optically detected magnetic resonance and embodiments thereof.

2. Description of Related Art

Significant progress in recent years in scanning tunneling microscopy (STM) and atomic force microscopy (AFM) have had a revolutionary impact in the direct imaging of atomic scale structure. Usually, STM and AFM devices are used for imaging of surface structures and cannot provide information about three-dimensional structures which are of the greatest interest in nano-technology, structural biology, biochemistry, and related fields of science. Magnetic resonance force microscopy (MRFM) was designed to meet the demands for imaging technology to be (1) nondestructive, (2) three-dimensional, (3) Angstrom-scale spatial resolution, and (4) capable of imaging individual biological molecules in situ. The recently developed techniques that demonstrate the highest sensitivity and spatial resolution are MRFM and optically detected magnetic resonance (ODMR). Significant progress in MRFM has been made since the first experiment, which was performed at IBM by a team led by Rugar. Today MRFM promises to achieve single spin sensitivity with several nanometer spatial resolution.

The main achievements in MRFM method are related to transfer of the detection of a very weak microwave signal to the detection of the mechanical oscillation of a micro-cantilever. Another option to enhance the sensitivity is transfer of the microwave signal to the optical domain, which is realized in the ODMR method. Related single spin experiments were independently performed in 1993 by two groups led by Moerner and Orrit. Today the principles of detection of a single spin based on ODMR are well established. The limitation of the lateral resolution of ODMR is related to the size of the light spot. The highest resolution is obtained by a near-field scanning optical microscope (NSOM), which has a light spot size of about 30-50 nm. Another limitation of the ODMR technique is that the unpaired electron has to be a part of a molecule, which absorbs or emits light.

BRIEF SUMMARY OF THE INVENTION

To improve the lateral resolution of the magnetic force resonance microscopy (MRFM) method, a new approach is described based on optically detected magnetic resonance (ODMR). In this approach, a photoluminescent nanoparticle is located in the tip apex of an atomic force microscope (AFM), a scanning tunneling microscope (STM) or a near-field scanning optical microscope (NSOM) and exhibits optically detected magnetic resonance in the vicinity of unpaired electron spins or nuclear magnetic moments in the sample material. The resolution of this method is related to the size of the photoluminescent probe, which is typically in the range of 1-10 nanometers or even of Angstrom scale when a single fluorescent molecule is used as a probe. The described spin microscope has demonstrated nanoscale lateral resolution and single spin sensitivity for the AFM and the STM embodiments. Among the most promising applications of the subject invention include spatial mapping of interfacial magnetism in nano-structures, imaging of three dimensional bio-molecular structures such as proteins/DNA/RNA complexes, non-demolition measurement of single spin state represented qubit in a quantum computer, and other uses as will become apparent from the detailed description of the invention.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

Figure 1:
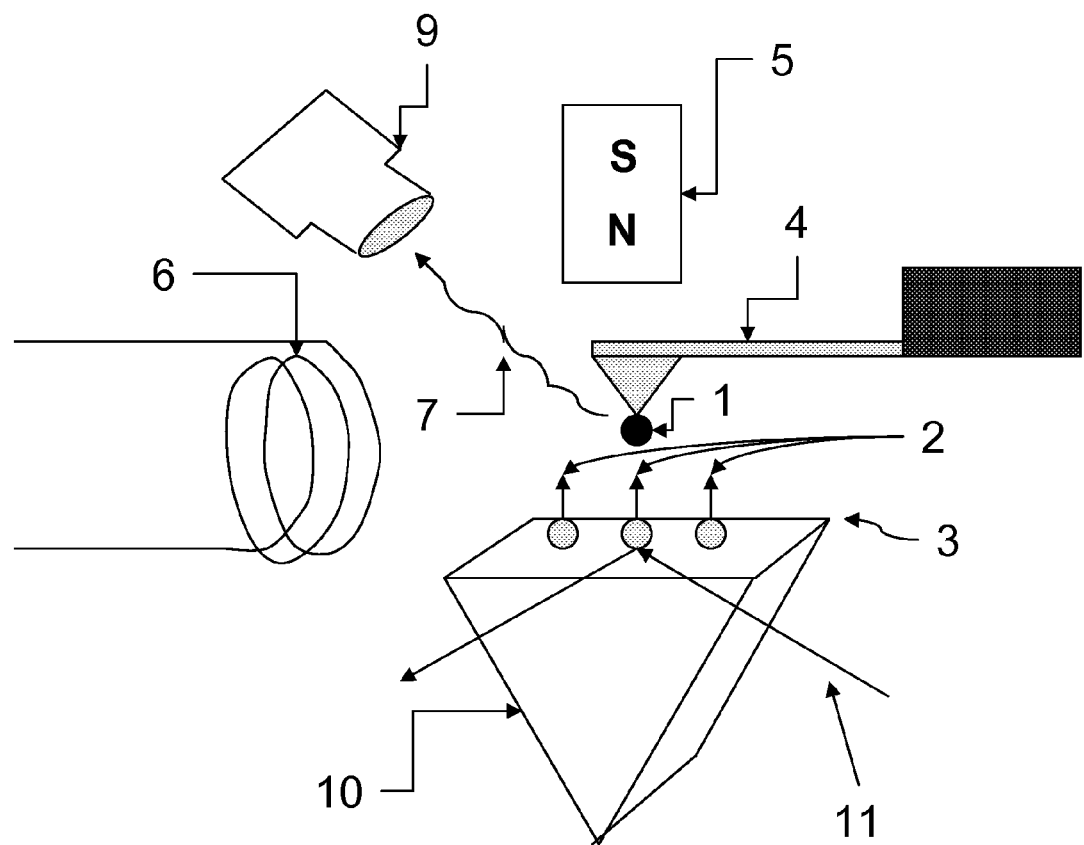
FIG. 1 is a schematic view of an optically detected magnetic resonance (ODMR)-based scanning microscope utilizing the atomic force microscope (AFM) and the near-field scanning optical microscope (NSOM) methods.

In the present invention a modification of the optically detected magnetic resonance (ODMR) technique is described which is free from the limitations of the conventional ODMR method. In this approach a photoluminescent nanoparticle 1 or other photoluminescent center located on the tip apex of a micro-cantilever 4 exhibits ODMR in the vicinity of unpaired electron spins 2 or nuclear magnetic moments in the sample 3. We have identified several approaches to this spin microscope based on ODMR, the general layouts of which are shown in FIGS. 1, 3-5. FIG. 1 presents a design based on the apertureless scanning optical microscope, which exploits the highly sensitive atomic force microscope (AFM) tip modified by implanting a nano-size photoluminescent particle 1 in the apex of the tip. The sample 3 material to be observed is located in close proximity to the tip-on-cantilever system, and a permanent magnet 5 is placed nearby. A nearby radio-frequency (rf) coil 6 produces an oscillating field at the frequency resonant with the transition between the magnetic sub-levels of the photoluminescent 7 nanoparticle. As an alternative to the nanoparticle, another photoluminescent center located in the tip apex which exhibits ODMR in the vicinity of unpaired electron spins or nuclear magnetic moments in the sample may be used. The nanoprobe absorption in an evanescent laser field could be significantly enhanced at the sharp apex of the silicon tip. As has been demonstrated by the JILA/NIST group, the combination of AFM with near-field optical scanning microscope (NSOM) method exhibits nano-scale spatial resolution and a significant increase in the detection 9 sensitivity when compared with utilizing the standard NSOM method alone.

Figure 2:
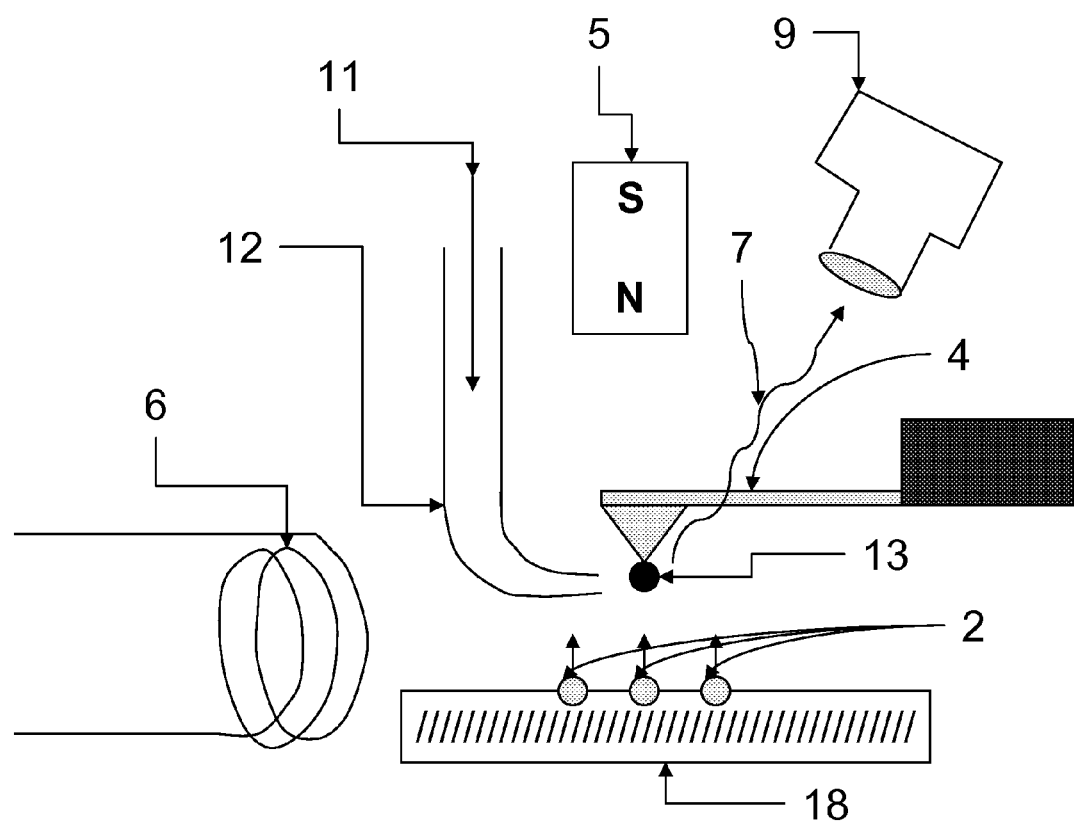
FIG. 2 is a schematic view of an optical detected magnetic resonance (ODMR)-based scanning microscope illuminated through an optical fiber.
Figure 3:
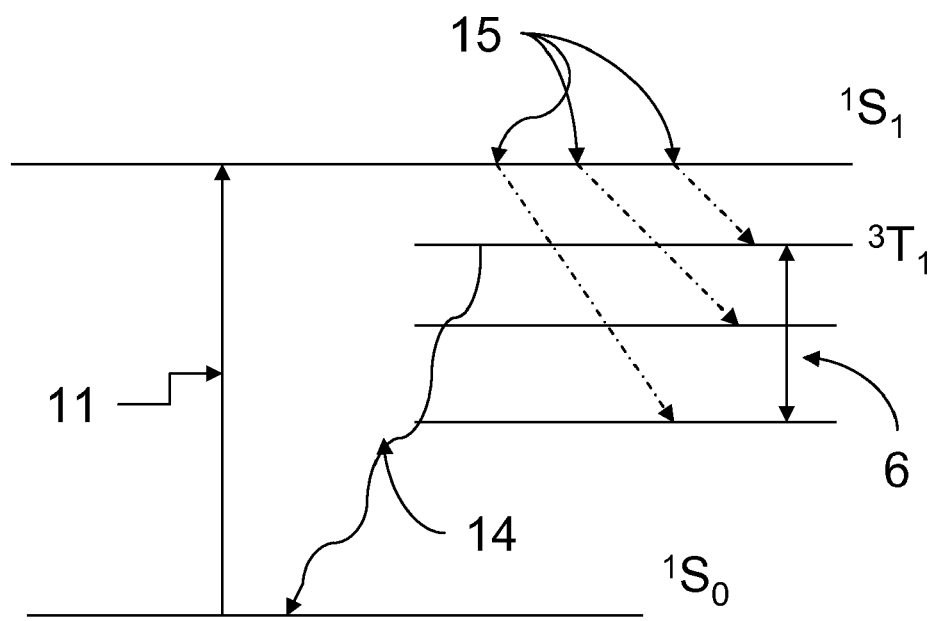
FIG. 3 is a schematic representation of the energy level diagram and optically detected magnetic resonance (ODMR)-based transitions of a nanoparticle.

To avoid the restrictions related to the necessity to mount the sample 3 on the prism 10, as seen in FIG. 1, one uses a design in which the excitation light 11 comes through an optical fiber 12. See FIG. 2. Such fiber could be a conically tapered fiber, which provides an evanescent field, or a round cross-sectional fiber as well, could be used. The resolution of this method is related to the size of the photoluminescent nanoprobe, which is typically in the range of 1-10 nm, or even of Ångström-scale when a single fluorescent molecule is used as a probe. The application of a fluorescent probe for nanometer scale lateral resolution was first proposed and experimentally demonstrated by the team led by Letokhov. In their approach, local fluorescent probes were employed for the fluorescent resonance energy transfer, where the donor molecules, located in the tip apex, were used to excite the fluorescence of an acceptor at the center of the sample.

Recent progress in the photoluminescence efficiency of semiconductor nanoparticles has catalyzed a broad spectrum of applications of these particles as luminescent nanoprobes 13. Semiconductor nanocrystals with nanometer diameters exhibit high quantum yields, typically over 50%, and high stability. In a semiconductor, quantum dot confinement leads to a replacement of continuous bands of energy by molecular-like energy levels structure. As was demonstrated for single molecules and nanostructures, the sensitivity of the ODMR method to the external magnetic field is higher for narrower photoluminescence spectrum substructure.

The theory of the spectrum of quantum dots shows that the ODMR spectrum depends on the mutual hole-electron interaction in the excitation. The hole and electron spins 15 create manifolds corresponding to singlet (S=0) or triplet (S=1) spin state or other type manifolds depending on the anisotropy of interaction. The spectroscopic scheme of ODMR presented in FIG. 3, comprises the optical transition $^1S_0$ to $^1S_1$ corresponding to excitation 11 with absorption of a photon from the laser field, the non-radiant transition to the manifold of the upper luminescent levels ($^3T_1$), and the luminescence 14 transition $^3T_1$ to $^1S_0$. The permanent magnetic field 5 changes the energy splitting of magnetic sublevels, and the rf field 6 induces transitions between sublevels, which are monitored 9 as increasing or decreasing of the photoluminescence 7 intensity. Note, that in the case of a single molecule as a probe 16, the photoluminescence is either a result of singlet-singlet luminescent transition $^1S_0$ to $^1S_1$ or emission which could be observed due to triplet-singlet optical phosphorescent transition $^3T_1$ to $^1S_0$. The sensitivity of the described scanning microscopy method is strongly dependent on the sharpness of the spectral structures measured in ODMR experiments.

There are two types of measurements possible. In the first type of measurement, the frequency of oscillating magnetic field 6 is fixed and the external permanent magnetic field 5 is varied. In the second type of measurement, the permanent magnetic field 5 is fixed and the frequency of oscillating magnetic field 6 is varied in the vicinity of the resonance frequency. Experiments with variable permanent magnetic field 5 demonstrate rather sharp spectral structures in the range 0.1-0.002 T at sample 18 temperatures of about 4° K.

Another technique is to use dye molecules as the nanoprobe 19. It is well known that at low temperature dye molecules have a very narrow ODMR width of about $10^{-3}$ T. Our analysis of the dependence of the sensitivity on geometry shows that at optimal conditions on ODMR of a nano-size probe can sense the magnetic field of a single electron spin. To estimate the sensitivity limit of an ODMR-based scanning microscope, one assumes that the diameter of the nanoprobe 13 is 1 nm; the distance between the nano-probe edge and the sample 18 surface is 5 Å; and in a radius of several nm there is only one unpaired spin. This spin is oriented perpendicular to the surface. The magnetic field from the single spin is given by $B_s=(\mu_0/4\pi)(3n(mn)-m)/r^3$. When we substitute $m=-(\frac{1}{2})g_e\mu_b=-9.28\times10^{-24}$ J/T, $\mu_0/4\pi=10^{-7}$ N/A$^2$, we get $B_s=1.5\times10^{-2}$ T. This value of the magnetic field of individual spin is larger than the most narrow range of the ODMR spectrum, and can be detected by measurement of the resonance shift.

Continuing progress of nanotechnology including spintronics and quantum information processing, based on the solid state quantum computer, has brought significant attention to the problem of measurements of magnetic properties of materials with sub-nanometer spatial resolution. For quantum computing applications, the two states of an individual spin represent a qubit. It would be desirable in this application that the procedure of measurement of the static magnetic field of a single spin does not perturb its quantum state and could be considered as an example of a non-demolition measurement of a quantum object. However, this property depends strongly on the quantum nature of excitation in the nanoprobe, and needs detailed consideration, which lies outside the scope of the present invention.

Figure 4:
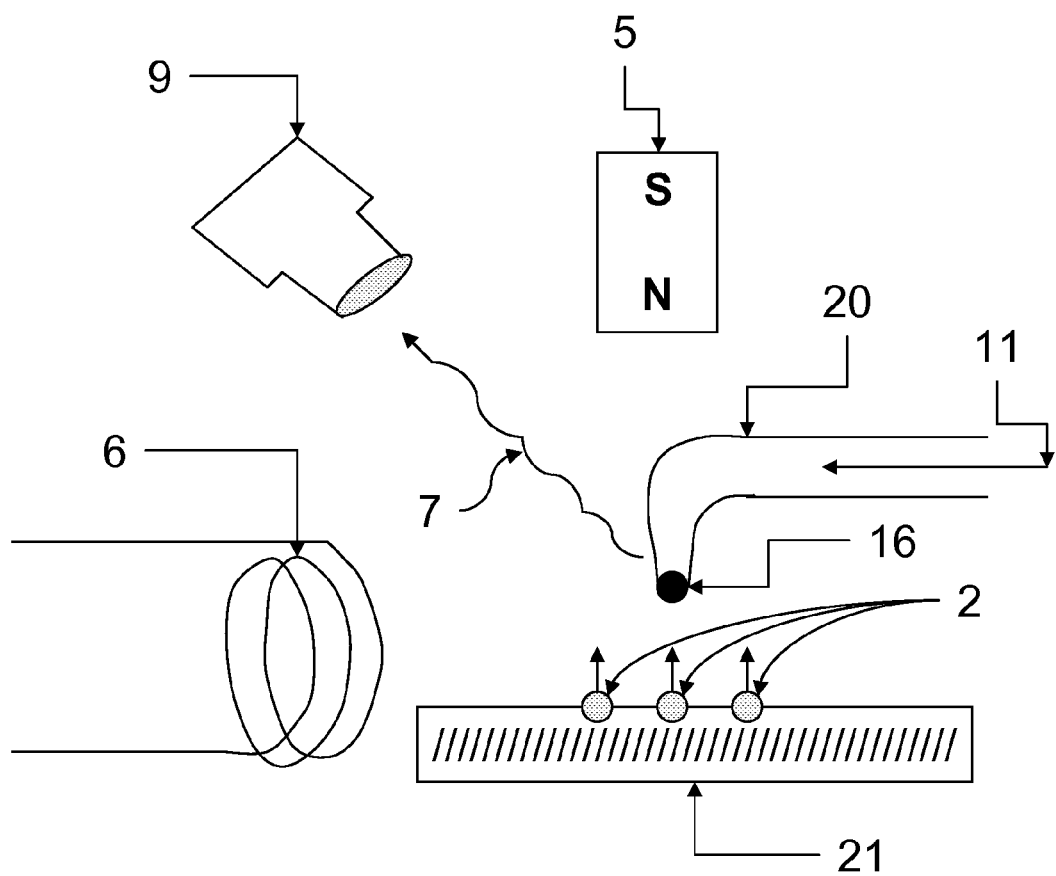
FIG. 4 is a schematic view of the optically detected magnetic resonance (ODMR)-based scanning microscope incorporating use of a cantilevered optical fiber.
Figure 5:
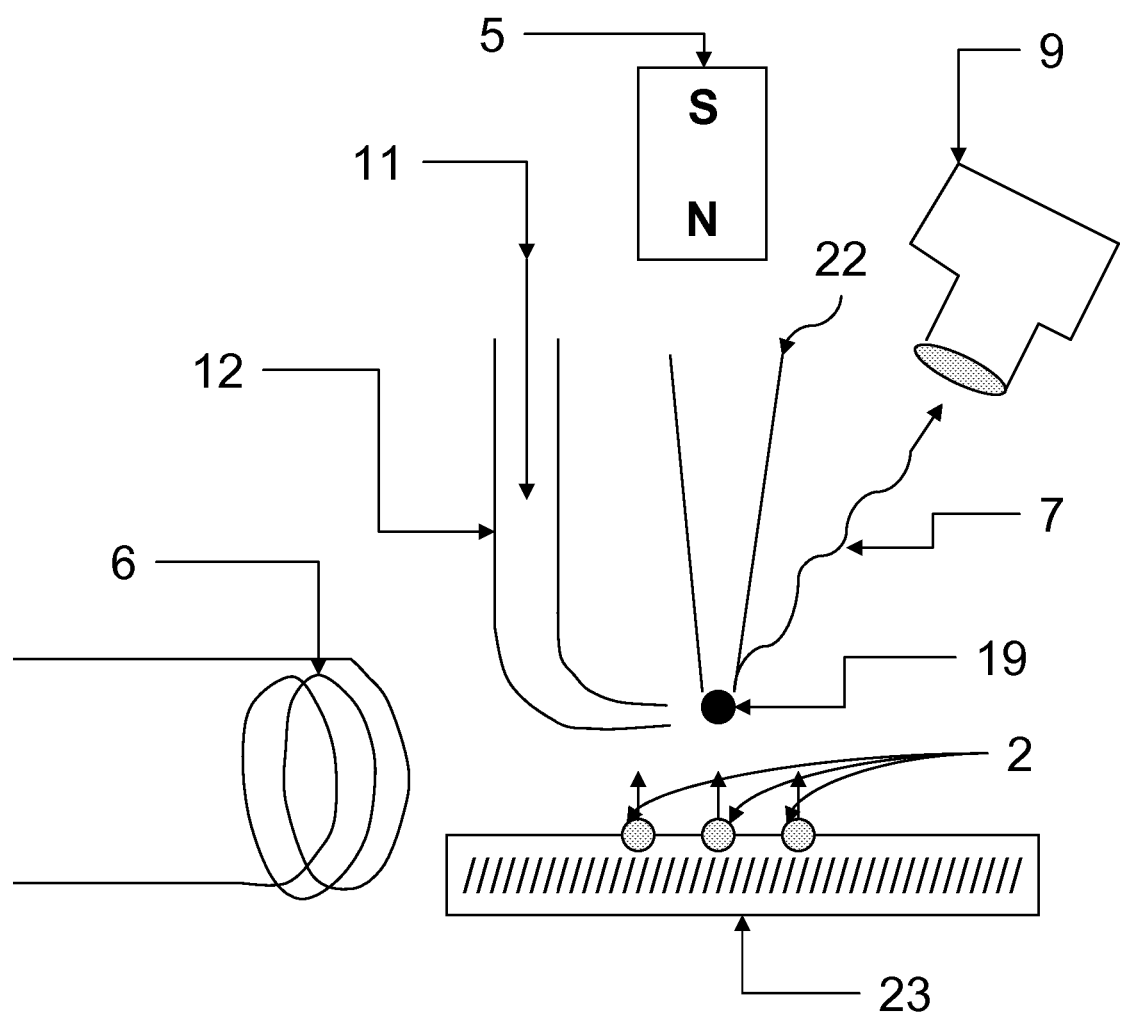
FIG. 5 is a schematic view of the optically detected magnetic resonance (ODMR)-based scanning microscope utilizing the scanning tunneling microscope (STM) method.

A scheme with spatial resolution of several tens of nanometers is presented in FIG. 4. The tip of a cantilevered optical fiber 20, such as developed by Nanonics Imaging, is modified by implantation of a photoluminescent nanoparticle 16 in the apex. This scheme may be used in combination with an opaque sample 21. The resolution obtained using this method is limited by the accuracy of positioning of the cantilevered fiber 20, which could be in a range of tens of nanometers. FIG. 5 presents a scheme which utilizes a scanning tunneling microscope (STM). The STM tip 22 has a nanoprobe 19 attached to the apex of the tip. The sample 23 is characterized by its conductivity. The resolution obtained using this method is limited by the size of the nanoprobe. It should be understood that any of the photoluminescent nanoprobes 1, 13, 16, 19 and any of the sample materials 3, 18, 21, 23 which have been previously described and are variously represented in the FIGS. 1, 2, 4 and 5 may be utilized interchangeably with any of the microscope embodiments presented herein.

In conclusion, the subject invention relates to a scanning magnetic microscope which incorporates a photoluminescent nanoprobe implanted in the apex of the tip of an AFM, STM, or NSOM microscope, and exhibits ODMR. The described spin microscope has demonstrated nanoscale lateral resolution and single electron spin sensitivity for the AFM and STM embodiments. Although the invention has been described in detail with particular reference to these embodiments, other embodiments can achieve the same results. Variations and modifications of the present invention will be obvious to those skilled in the art and it is intended to cover in the appended claims all such modifications and equivalents. The entire disclosure of all references, applications, patents, and publications cited above are hereby incorporated by reference.

REFERENCES

1. D. Rugar, C. S. Yannoni, and J. A. Sidles, Nature, 360, 563 (1992).
2. J. Köhler, J. A. J. M. Disselhorst, M. C. J. M. Donckers, E. J. J. Groenen, J. Schmidt, and W. E. Moerner, Nature 363, 242 (1993)
3. J. Wrachtrup, Nvon Borczyskowski, J. Bernard, M. Orritt, and R. Brown, Nature, 363, 244 (1993)
4. H. F. Hamann, A. Gallagher, and D. J. Nesbitt, Appl. Phys. Lett., 73, 1469 (1998)
5. S. K. Sekatskii and V. S. Letokhov, JETP Lett., 63, 319 (1996).
6. G. T. Shubeita, S. K. Sekatskii, G. Dietler, and V. S. Letokhov, Appl. Phys. Lett., 80, 2625-2627 (2002).
7. G. Belomoin, J. Therrien, A. Smith, S. Rao, R. Twesten, S. Chaieb, M. H. Mayfeh, L. Wagner, and L. Mitas, Appl. Phys. Lett., 80, 841-843 (2002)
8. Y. Q. Wang, G. L. Kong, W. D. Chen, H. W. Diao, C. Y. Chen, S. B. Zhang, and X. B. Liao, Appl. Phys. Lett., 81, 4174-4176 (2002)
9. M. Bayer, O. Stern, P. Hawrylak, S. Fafard, and A. Forchel, Nature, 405, 923 (2000)
10. E. Lifshitz, I. Dag, and I. D. Litvin, G. Hodes, J. Phys. Chem. B, 102, 9245 (1998)
11. Zurauskiene, G. Janssen, E. Goovaerts, A. Bouwen, D. Schoemaker, P. M. Koenraad, and J. H. Wolter, Phys. Stat. Sol. B, 224, 551 (2001).
12. B. Chernobrod and G. Berman, J. Appl. Phys., 97, 014903 (2005).

We claim:

1. A scanning magnetic microscope comprising:
   an ultrasensitive micro-cantilever onto the free end of which is fixed a photoluminescent material which exhibits an optically detectable magnetic resonance;
   a sample of dilute paramagnetic particles exhibiting electron spins which is closely positioned, in the range of tens of nanometers, to said photoluminescent material;
   a permanent magnet placed nearby for inducing an external magnetic field upon said photoluminescent material and said sample of dilute paramagnetic particles;
   a radio frequency coil placed nearby for inducing an external radio frequency field upon said photoluminescent material and said sample of dilute paramagnetic particles;
   an optical fiber placed in close proximity to said photoluminescent material for introducing an evanescent laser exciting light upon said photoluminescent material at a frequency resonant with the transition between the magnetic sublevels of said photoluminescent material; and
   a detector, positioned at a 45 degree angle to said photoluminescent material and said sample of dilute paramagnetic particles in both plan and elevation views, capable of optically recognizing the photoluminescent intensity of transition emissions given off by said photoluminescent material when excited.

* * * * *